(12) United States Patent
Patil et al.

(10) Patent No.: US 8,792,102 B2
(45) Date of Patent: Jul. 29, 2014

(54) INTERFEROMETRIC SPECTRAL IMAGING OF A TWO-DIMENSIONAL ARRAY OF SAMPLES USING SURFACE PLASMON RESONANCE

(75) Inventors: Abhijit Vishwas Patil, Bangalore (IN); Sandip Maity, Bangalore (IN); Veera Venkata Lakshmi Rajesh Langoju, Bangalore (IN); Anusha Rammohan, Bangalore (IN); Sameer Dinkar Vartak, Bangalore (IN); Umakant Damodar Rapol, Pune (IN)

(73) Assignee: General Electric Company, Niskayuna, NY (US)

( * ) Notice: Subject to any disclaimer, the term of this patent is extended or adjusted under 35 U.S.C. 154(b) by 849 days.

(21) Appl. No.: 12/914,622

(22) Filed: Oct. 28, 2010

(65) Prior Publication Data

US 2012/0105852 A1    May 3, 2012

(51) Int. Cl.
*G01J 3/45* (2006.01)
*G01N 21/47* (2006.01)
*G01N 21/25* (2006.01)
*G01N 21/45* (2006.01)
*B01L 3/00* (2006.01)
*G01N 21/03* (2006.01)
*G01N 21/05* (2006.01)
*G01N 21/55* (2014.01)

(52) U.S. Cl.
CPC ....... *G01N 21/253* (2013.01); *B01L 2300/0636* (2013.01); *B01L 3/5027* (2013.01); *B01L 2300/0829* (2013.01); *G01N 2021/0346* (2013.01); *G01N 21/05* (2013.01); *B01L 2300/089* (2013.01); *B01L 3/5085* (2013.01); *G01N 21/554* (2013.01); *G01N 21/45* (2013.01); *G01N 21/553* (2013.01)
USPC ........................................... 356/456; 356/445

(58) Field of Classification Search
USPC .......... 356/445, 456, 479, 497, 481, 504, 517
See application file for complete search history.

(56) References Cited

U.S. PATENT DOCUMENTS

| | | | |
|---|---|---|---|
| 5,994,690 A | 11/1999 | Kulkarni et al. | |
| 6,330,062 B1 * | 12/2001 | Corn et al. | 356/445 |
| 6,833,920 B2 * | 12/2004 | Rassman et al. | 356/369 |
| 6,862,094 B2 | 3/2005 | Johansen et al. | |
| 6,970,249 B1 * | 11/2005 | Lipson et al. | 356/445 |
| 7,084,980 B2 * | 8/2006 | Jones et al. | 356/445 |
| 7,365,859 B2 * | 4/2008 | Yun et al. | 356/497 |
| 7,518,728 B2 * | 4/2009 | Koo | 356/456 |
| 7,633,627 B2 | 12/2009 | Choma et al. | |
| 7,639,355 B2 * | 12/2009 | Fattal et al. | 356/301 |
| 7,659,063 B2 | 2/2010 | Kris et al. | |
| 8,233,152 B2 * | 7/2012 | Suehira | 356/497 |
| 8,289,522 B2 * | 10/2012 | Tearney et al. | 356/479 |

(Continued)

OTHER PUBLICATIONS

Search Report and Written Opinion from corresponding PCT Application No. PCT/SE2011/051265 dated Feb. 28, 2012.
Piliarik et al., "A new surface plasmon resonance sensor for high-throughput screening applications", Biosensors and Bioelectronics 20, No. pp. 2104-2110, Apr. 15, 2005.

(Continued)

*Primary Examiner* — Hwa Lee
(74) *Attorney, Agent, or Firm* — Jenifer E. Haeckl

(57) ABSTRACT

A detection system for a two-dimensional (2D) array is provided. The detection system comprises an electromagnetic radiation source, a phase difference generator, a detection surface having a plurality of sample fields that can receive samples, and an imaging spectrometer configured to discriminate between two or more spatially separated points.

20 Claims, 12 Drawing Sheets

(56) References Cited

U.S. PATENT DOCUMENTS

| | | | | |
|---|---|---|---|---|
| 2003/0219809 | A1* | 11/2003 | Chen et al. | 435/6 |
| 2004/0191815 | A1* | 9/2004 | Kyo et al. | 435/6 |
| 2005/0018949 | A1* | 1/2005 | Yan | 385/14 |
| 2005/0194523 | A1 | 9/2005 | VanWiggeren et al. | |
| 2007/0046943 | A1* | 3/2007 | VanWiggeren et al. | 356/445 |
| 2007/0166763 | A1* | 7/2007 | Ho et al. | 435/7.1 |
| 2007/0229801 | A1* | 10/2007 | Tearney et al. | 356/73 |
| 2008/0218860 | A1* | 9/2008 | Robertson | 359/534 |
| 2010/0067015 | A1* | 3/2010 | Matsushita et al. | 356/445 |

OTHER PUBLICATIONS

Homola et al. "Multi-analyte surface plasmon resonance biosensing", Methods 37, pp. 26-36, 2005.

Otsuki et al. "Wavelength-scanning surface plasmon resonance imaging". Appl. Opt. 44(17), pp. 3468-3472, Jun. 10, 2005.

Sims et al., "The specific molecular identification of life experiment (SMILE)", Planetary and Space Science, vol. 53, No. 8, pp. 781-791, Jul. 1, 2005.

Erickson et al., "Nanobiosensors: optofluidic, electrical and mechanical approaches to biomolecular detection at the nanoscale", Microfluid Nanofluid 4, pp. 33-52, Aug. 8, 2007.

* cited by examiner

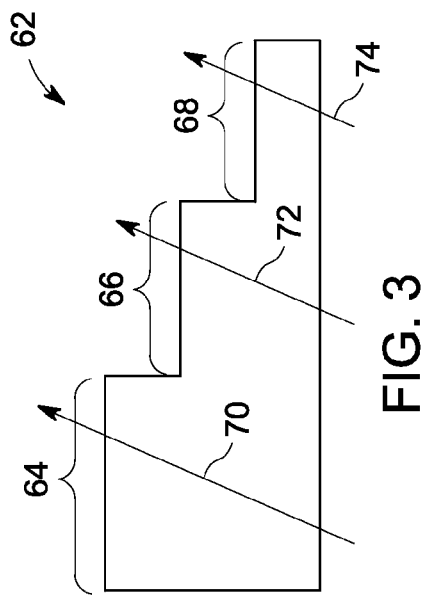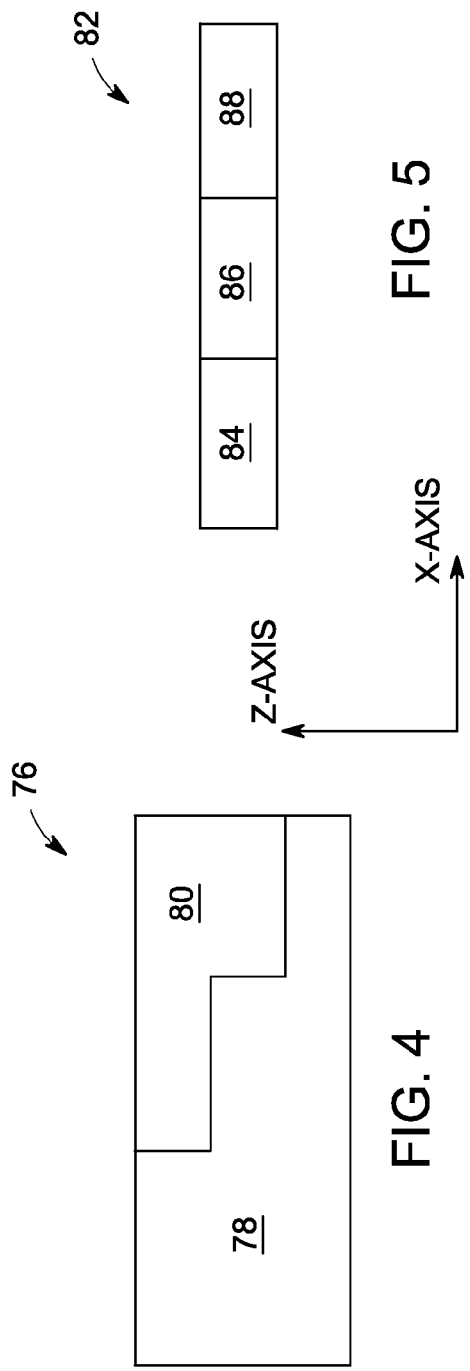

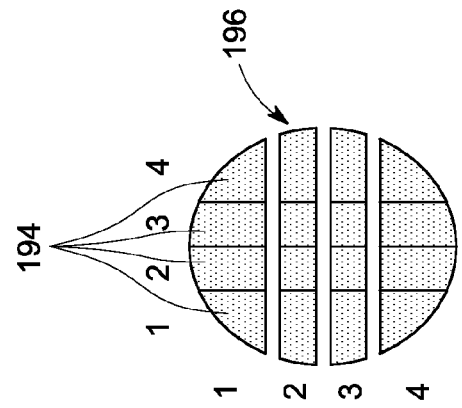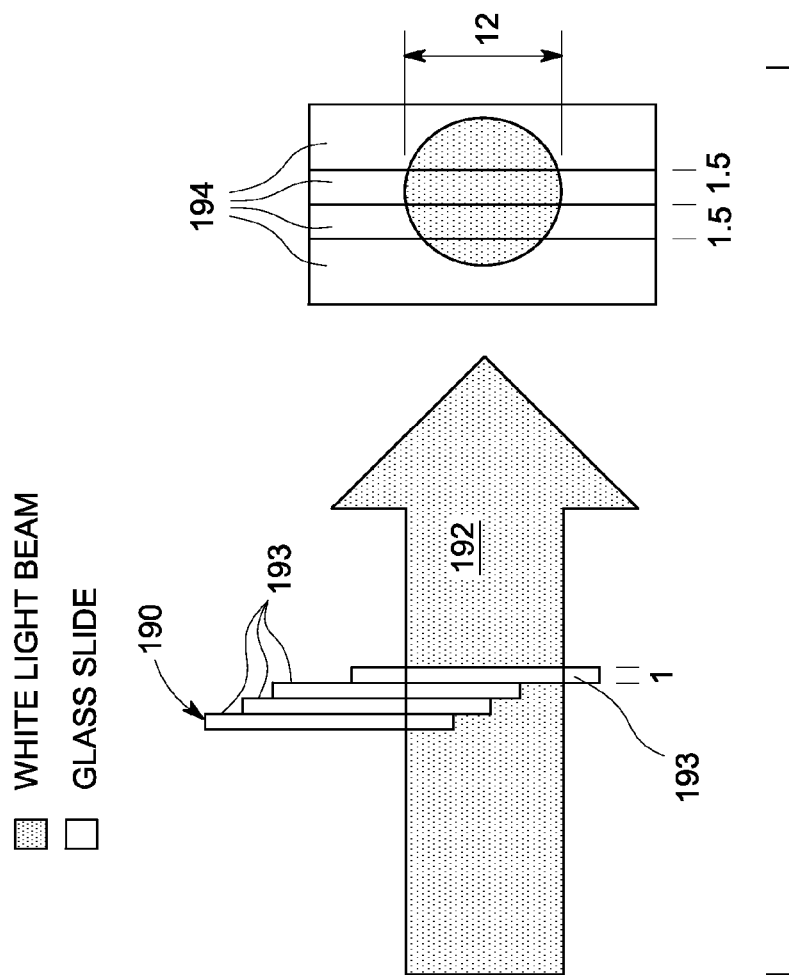
FIG. 13
FIG. 12

INTERFEROMETRIC SPECTRAL IMAGING OF A TWO-DIMENSIONAL ARRAY OF SAMPLES USING SURFACE PLASMON RESONANCE

BACKGROUND

The invention relates to detection and imaging, and more particularly to systems and methods for detection and imaging of two-dimensional (2D) sample arrays.

Surface plasmon resonance (SPR) is detected using a spectroscopy technique by sensing refractive index changes near the surface of a metal film. High sensitivity of refractive index changes provides a platform for the observation and quantification of chemical reactions at the metal/solution interface. The SPR technique can be used in a wide variety of chemical systems, including bio sensors.

Typically, SPR sensors employ a prism that supports a thin metal layer. The sample to be detected, such as a ligand, is immobilized on one side of the metal surface to form a modified metal surface. A reflection spectrum of the modified metal surface is measured by coupling in light and measuring the intensity of the reflected light as a function of the angle of incidence or the wavelength.

In SPR, usually a single sample is monitored at a given time. In case of multiple samples, the time required for detection increases, with the increase in the number of samples. Scanning angle SPR is typically used for scanning more than one sample. Typically, in a scanning angle SPR the intensity of the reflected light is measured as a function of the angle of incidence. The light is directed from a light source through a prism onto the modified metal surface. As the angle of incidence of the light is varied, at a particular angle, the surface plasmon resonance is observed as a sharp dip in the intensity of the light internally reflected within the prism at that particular angle of incidence. The angle of incidence at which resonance occurs is affected by the refractive index of the thin sample layer disposed on the metal film. The angle of incidence corresponding to resonance is thus a direct measure of the characteristics of the thin sample layer. Disadvantageously, the scanning angle SPR is limited over a narrow angular range. The limited angular range restricts the range of sample area and in some cases it also restricts refractive index that can be measured. In addition, some systems achieve 2D SPR imaging by mechanically scanning the light source. Lack of precision in the angular control while scanning the angular range affects the reproducibility of the SPR measurement results. Further, mechanical type of scanning increases complexity of the instrument.

Non-mechanical methods for scanning angles may have higher sensitivity, however, the SPR image frame rate is still less than the actual frame rate of the camera. This is because each point in time corresponds to single angle and scanning angle in time reduces actual frame rate.

Therefore, it is desirable to have improved systems and methods for detecting and imaging of 2D arrays of samples.

BRIEF DESCRIPTION

In one embodiment, a detection system for a two-dimensional (2D) array is provided. The detection system comprises an electromagnetic radiation source, a phase difference generator, a detection surface having a plurality of sample fields that can receive samples, and an imaging spectrometer configured to discriminate between two or more spatially separated points.

In another embodiment, a two-dimensional (2D) surface plasmon resonance (SPR) imaging system is provided. The system comprises a SPR surface having a 2D array of samples disposed in one or more corresponding sample fields, a broadband light source that illuminates one or more of the sample fields, a phase difference generator that introduces differences in pathlengths of resultant sample beams reflected from the 2D array of samples, and a detector that receives the resultant light beams from the 2D array of samples.

In yet another embodiment, a method for simultaneous imaging of samples in a 2D array is provided. The method comprises providing a sample beam and a reference beam, illuminating the samples in the 2D array with the sample beam to produce a resultant sample beam, introducing a path difference in one of the reference beam or the resultant sample beam, interfering the resultant sample beams with the reference beam to form interference spectra, spectrally separately acquiring the interference spectra, reconstructing an image of the 2D array using a Fourier transform of the acquired interference spectra.

DRAWINGS

These and other features, aspects, and advantages of the invention will become better understood when the following detailed description is read with reference to the accompanying drawings in which like characters represent like parts throughout the drawings, wherein:

FIGS. 3-5 are cross-sectional drawings of embodiments of phase difference generators of the invention;

FIG. 12 is a cross-sectional view of an arrangement having a phase plate disposed in a path of a beam to divide a beam area in four regions;

FIG. 13 is a schematic drawing of the beam area of FIG. 12, where the beam area is further divided into four regions to produce a 4×4 spot array;

DETAILED DESCRIPTION

One or more embodiments of the system of the invention generally carry out simultaneous detection of two or more samples disposed in a two dimensional (2D) array. The system may also be configured to image the samples as well. In one embodiment, the 2D array may be reconstructed by introducing a spectral separation in the 2D array in a first direction (e.g., x-direction), and imaging the 2D array in a second direction (e.g., y-direction), where the second direction is different from the first direction. Advantageously, the samples in the 2D array may be detected and imaged in a single shot or frame. Thus, the method may be incorporated into a high throughput sample detection and imaging system.

In certain embodiments, the system for simultaneous detection of a 2D array of samples comprises a detection surface having the 2D array of samples, an electromagnetic radiation source, a phase difference generator, and a 2D detector that is able to discriminate between two or more spatially separated points. The detector may be used to produce an image of the detected 2D array.

Figure 1:
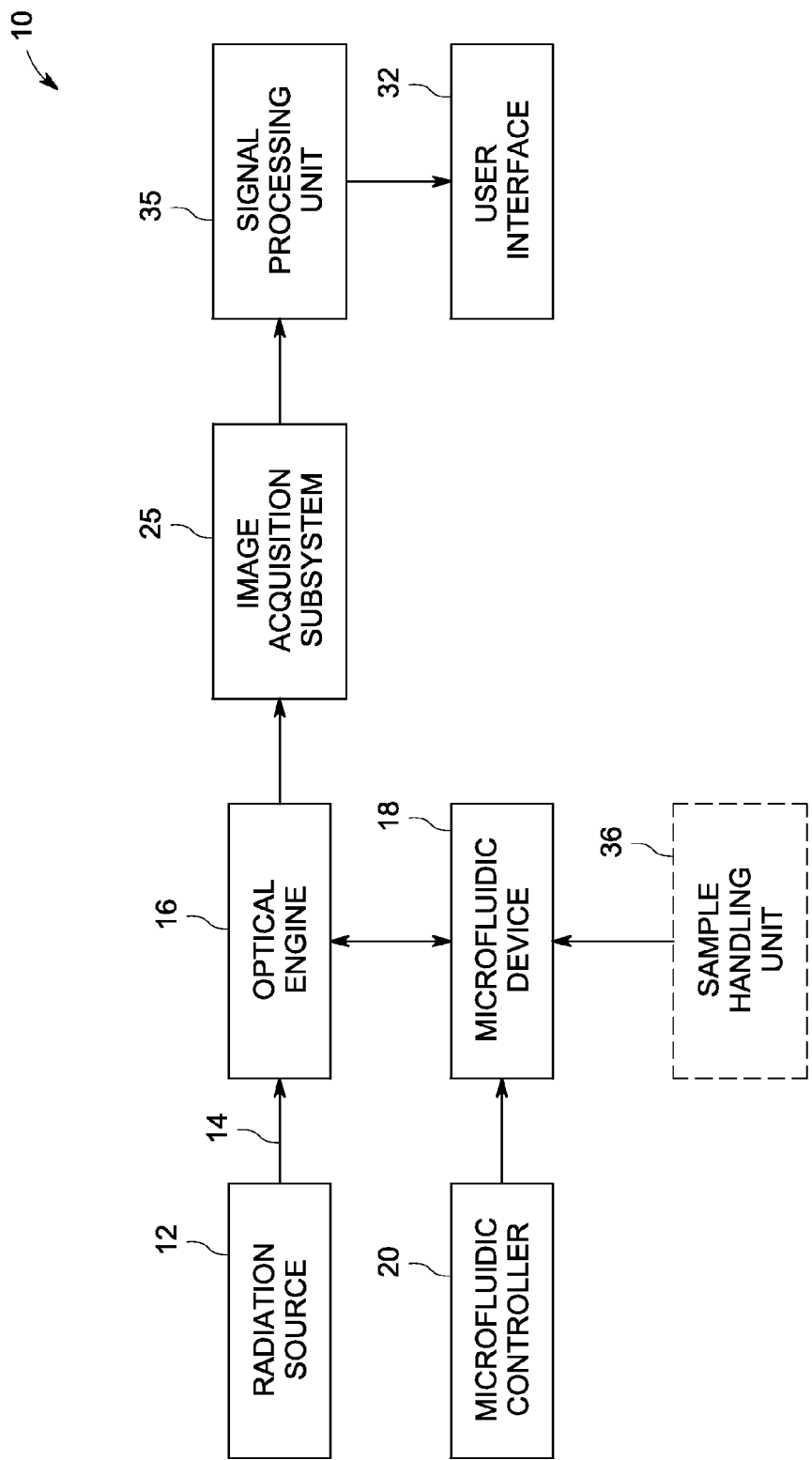
FIG. 1 is a flow chart of an embodiment of a detecting and imaging system of the invention for simultaneous detection of 2D array of samples.

FIG. 1 illustrates an example of a detecting and imaging system 10 for simultaneously detecting a 2D array of samples. The system 10 comprises an electromagnetic radiation source 12 for irradiating the 2D array of samples with electromagnetic radiation 14. The radiation source 12 may produce visible light, or near infrared light depending on the types of samples to be detected. The radiation source 12 may include a light emitting diode, a surface light emitting diode, a tungsten lamp, a white light source, a broadband light source, a xenon lamp, a metal halide lamp, or a phosphor source. As used herein, the term "broadband light source" refers to a light source that emits a continuous spectrum output over a range of wavelengths at any given point of time.

The radiation 14 from the radiation source 12 is directed to an optical engine 16. The optical engine 16 comprises a detection surface (not shown). A 2D array of samples is disposed on the detection surface. A microfluidic device 18, such as a microfluidic chip, may be operatively coupled to the detection surface to provide the samples to the detection surface. A microfluidic controller 20 may be provided to control the microfluidic operations of the microfluidic device 18. Optionally, a sample handling unit 36 may be used to transfer, or store samples from/to the microfluidic device 18.

The optical engine 16 may have either be in a Michelson or Mach Zhender interferometer configuration. The optical engine 16 comprises a phase difference generator for inducing phase difference in the radiation illuminating the sample with respect to the reference beam. The optical engine 16 comprises an optical arrangement for directing the radiation to a 2D array of samples and a reference. The samples are detected by analyzing an interference spectrum formed by interfering the sample radiation with a reference radiation. The interference spectrum from the optical engine 16 is received by the image acquisition unit 25. The image acquisition unit 25 acquires image data that includes interference in spectral domain. The image acquisition unit 25 may include a combination of a detector and a grating. In one embodiment, the grating comprises 3600 lines per mm, however, other values of grating lines per mm may also be selected. The grating may be tilted at a determined angle to obtain additional spatial separation of frequencies. The image acquisition unit 25 may include additional optical elements such as lens for collimating or focusing the radiation. The acquired image may be processed using the signal processing unit 35. A graphical user interface (GUI) 32 may be used to provide a user interface to allow the user to interact with the detection system 10.

Figure 2:
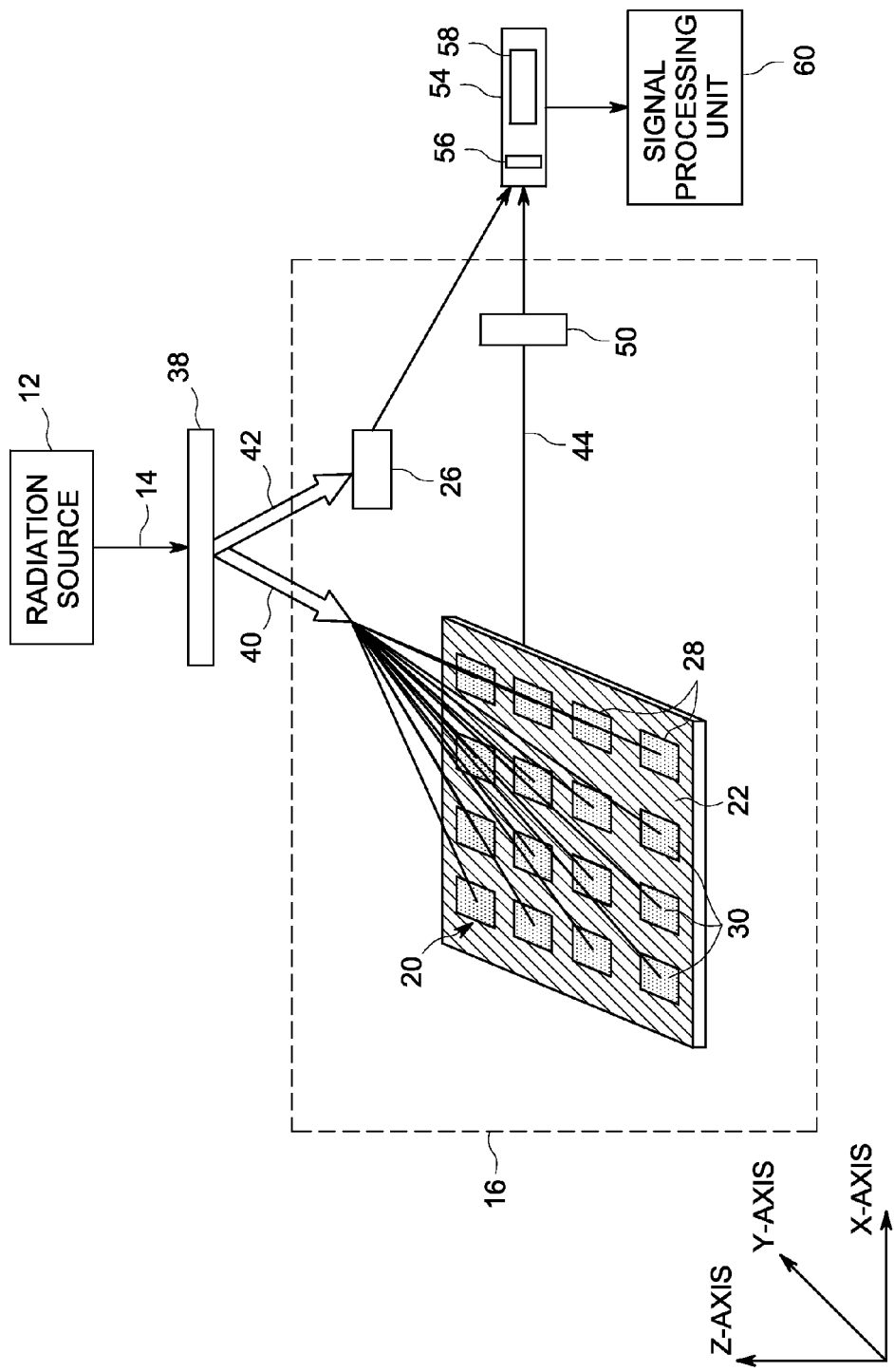
FIG. 2 is a schematic drawing of an embodiment of an optical engine of the invention.

FIG. 2 illustrates an example of the optical arrangement within the optical engine 16. The optical engine 16 comprises an optical arrangement for directing a portion of the radiation 14 from the radiation source 12 to a 2D array 20 of samples 30. The 2D array 20 may be of varying sizes such as, but not limited to, a 4×4 array of samples, a 6×6 array of samples, or an 8×8 array of samples 30. The 2D array 20 is disposed on a detection surface 22. A beam splitter 38 is used to split the radiation 14 into the sample beam 40 and the reference beam 42. The sample beam 40 is directed towards the 2D array 20 of samples 30, and the reference beam 42 is directed towards the reference 26. The general direction from the radiation source 12 towards the detection surface 22 is referred to as a sample arm and the general direction from the radiation source 12 towards the reference 26 is referred to as a reference arm.

The 2D array 20 of samples 30 may be disposed on a detection surface 22. The detection surface 22 may comprise a plurality of sample fields 28 that contain the samples 30. The detection surface 22 may be a spectrally modifying surface that may reflect, absorb, or transmit at least a portion of the incident sample beam 40. The detection surface 22 may be varied depending on the detection techniques that are used. Non-limiting examples of the detection techniques may include surface plasmon resonance (SPR) such as but not limited to, localized surface SPR or a nano-grating SPR, or a reflectometric interference spectroscopy (RIfS). In case of localized surface SPR, the detection surface 22 may include a glass substrate having a metal coating. In case of RifS the detection surface 22 may include a glass surface. In case of nano-grating SPR, the detection surface 22, may include a glass surface having nano gratings.

The sample fields 28 on the detection surface 22 may be functionalized using ligand molecules. The ligand molecules may be present in the form of a layer or a coating, also referred to as a functionalized coating. In one embodiment, the detection may be based on the competitive binding of the sample to the binding sites of the ligand. Same or different ligands may be disposed in the different sample fields 28 of the 2D array 20. The ligands may be disposed in discrete areas (corresponding to sample fields 28 of the 2D array 20) to form an array of discrete sample-binding regions. The ligands may be disposed in discrete sample fields 28, such that one or more of the sample fields 28 comprise a ligand molecule different than the other regions. In one embodiment, all the different sample fields 28 may comprise different ligand molecules. The ligands may comprise one or more of a biopolymer, an antigen, antibody, nucleic acids and hormone ligands. In one example, for antibody binding measurements, an antigen may be immobilized on the sample field 28 and the detection surface may be exposed to a solution containing the antibody of interest, and binding proceeds.

The samples 30 may be chemical or biological samples. In one embodiment, the samples 30 may be chemically or biologically active samples. These chemically or biologically active samples 30 may produce a determined response when they come in contact with a chemical or a biological entity, respectively. In one example, the samples 30 may have a time constant optical property. The samples 30 may comprise optically active materials. In one example, the samples 30 may be able to absorb, transmit, or reflect the incident radiation.

In one embodiment, a plurality of flow cells of a microfluidic device (not shown) may be operatively coupled to the detection surface 22 to provide the samples 30 to the one or more sample fields 28 on the detection surface 22. Each flow cell may comprise at least one fluidic channel. Each flow cell may correspond to one or more sample fields 28 on the detection surface 22. For example, each of the fluidic channels may be aligned to a particular sample field 28. In embodiments where the different sample fields 28 may comprise different ligand molecules, the different sample fields 28 may be aligned with a corresponding fluidic channel having a corresponding ligand molecule.

Although not illustrated, optionally a definer component may be provided to define the geometry and the number of sample fields 28. Also, the contrast between the sample fields 28 and their intermediate regions may be determined by the definer component. In certain embodiments, a definer component may be disposed in selected regions of the detection surface 22. For example, the definer component may be disposed in regions around the sample fields 28. The regions having the definer component may not comprise the sample. In case of SPR imaging, the definer component may be used to create a contrast outside of surface plasmon resonance occurring in the SPR sensor surface areas (sample fields 28). The individual sample fields and the definer component surrounding the individual sensor fields are configured so that the reflectivity of the definer component is less than the reflectivity of the individual sample fields.

Simply, the definer component may be a patterned film of a suitable material. The definer component may include a light absorbing material. Suitable materials for the definer component may include layers of a light absorbing metal, or semiconductor, or polymer, such as photoresist polymers. In one embodiment, the sample fields 28 on the detection surface 22 may be defined by the definer component. That is, the definer component in conjunction with the detection surface 22 may define the sample fields 28 on the detection surface 22. For example, the definer component may form continuous raised structures on the detection surface 22, and areas enclosed by these raised structures may be defined as the sample fields 28. Positioning and adjusting the 2D array 20 of samples 30 may be done by selecting a suitable patterned film of the definer component. The creation of contrast enables the sample fields to be easily distinguished from the non-sample fields. In addition to distinguishing the sample fields 28 with the non-sample fields, the definer component may also minimize or prevent contamination between neighboring sample fields 28, or between the sample fields 28 and the detection surface 22. For example, the definer component may form elevations above the SPR sensor surface areas in the direction perpendicular to the substrate. In case of water based sample solutions, it is desirable for the definer component to be hydrophobic or hydrophobicized so that an aqueous solution is well contained within the sample fields 28 without the possibility of cross-contamination with neighboring samples 30.

In addition to or in place of the definer component, a filtering component (not shown) may be used to filter off or absorb any light that is not reflected from the sample fields 28. For example, the filtering component may block the light (e.g., by absorbing the light) reflected from the areas around the sample fields 28. The blocking of the undesired light reduces the load at the detector, and enhances the performance of the device by reducing the noise. The filtering component may be disposed anywhere in the sample arm. In one embodiment, the filtering component may be disposed closer to the detector 34 than the detection surface 22. In another embodiment, the filtering component may be disposed on the detection surface 22. In one embodiment, the filtering component may be made of the same material as the definer component. The filtering component may have the similar shape/pattern as the definer component. In one embodiment, the filtering component and the definer component may be integrated to form one structure. In this embodiment, the integrated structure may be made of light absorption material.

The sample beam 40 is directed to the 2D array of samples and interacts with the 2D array of samples 30. The resultant sample radiation, generally referred to by the reference numeral 44, may be a reflective radiation or a transmissive radiation produced by interaction of the incident sample beam 40 with the 2D array of samples 30. In one embodiment, the sample beam 40 is directed to a multi-spot generator optics to produce two or more spatially-spread discrete spots. The spatially-spread discrete spots are incident on the 2D array of samples 30. In one example, each of the spatially-spread discrete spots corresponds to a sample 30 in the 2D array 20.

The imaging of the 2D array 20 is obtained by reconstructing absorption spectrum of the samples 30 using a Fourier transform. The resultant sample radiation 44 from the various samples 30 needs to be separately identified by the detector 34 to identify the individual samples 30 in the 2D array 20. In certain embodiments, the 2D array 20 of samples 30 may be imaged in a single shot. The Fourier transform may be used to determine the spatially separated points (samples 30) from the acquired spectra without movement of any mechanical part or the reference beam, thereby improving the imaging speed.

Since a Fourier transform is applied to reconstruct the image of the sample fields 28, using a definer component may not be sufficient to distinguish between the individual samples 30 in the sample fields 28. In certain embodiments, phase difference may be introduced in the interference spectrum of the resultant sample beam 44 and the reference beam 42. The phase difference may be introduced either in the sample arm or the reference arm. That is, the phase difference may be introduced either in the reference beam 42 or the resultant sample beam 44 from the 2D array 20. For example, the resultant sample beam 44 may be passed through a phase difference generator 50 before reaching the detector 34. Although not illustrated, alternatively, the spectral separation may be obtained by passing the reference beam 42 through a phase difference generator. The phase difference generator 50 may be used to resolve the sample fields 28 in the 2D array. In some embodiments, the phase difference generator 50 may introduce a path length difference between the resultant sample beams received from the different samples 30. The path length difference may be translated in to phase difference in the interference spectrum. The phase difference thus obtained is used to spatially separate the different samples in the Fourier transform.

The phase difference may be introduced in a determined direction, and the imaging may be carried out in a direction different from the determined direction. Imaging in a direction different from that in which the phase difference is introduced, resolves the samples 30 in both x- and y-directions. In one example, the phase difference generator 50 may introduce a phase difference in a x-direction and the imaging may be done in a y-direction. In this example, the phase difference generator 50 facilitates resolving the samples 30 along the x-direction, and the detector resolves and spatially separates the samples 30 disposed along the y-direction.

In embodiment where the reference radiation is subjected to the phase difference generator 50, a condition for interference is generated by combining the reference radiation having the phase difference with the resultant radiation from the sample. Alternatively, in embodiment wherein the resultant radiation is subjected to the phase difference generator 50, a condition for interference is generated by combining the resultant sample radiation having the phase difference with the reference radiation. Because of the effect of this interference, the intensity of the beam received at the detector 34 depends on the difference in the path length of the beams in the two arms.

Although not shown, the optical engine 16 may also include other optical elements such as lens, filters, collimators, and the like. For example, a lens each may be disposed in the reference arm and the sample arm to direct the radiation to the detector.

In addition to the phase shift caused by the phase difference generator 50, the samples 30 disposed in the sample fields 28 may also produce phase shift in the resultant sample radiation. The phase shift produced by the sample, may be a fraction of the phase shift produced by the phase shift generator 50. The small phase shift component may shift the corresponding fringe in the interference pattern. The shift of the fringe corresponds to the properties of the sample 30 at that sample field 28. The additional shift in the resultant radiation caused by the sample 30 may facilitate determination of the chemical or optical properties of the sample 30.

The interference spectrum between the resultant sample radiation 44 and the reference beam 42 is analyzed and imaged using an imaging spectrometer 54. The imaging spectrometer 54 may include a spectrally separated 2D detector 58 and a grating 56. The spectral frequencies in the interference spectrum are separated using the 2D detector 58 and the grating 56. The detector 58 detects a change in the optical properties of the reflected light from the 2D array of samples 30. The detector 58 may detect the analytes concentration, or chemical or biological composition in the sample.

The detector 58 may be a photodetector, a spectrometer, or a charge-coupled device (CCD), complementary metal oxide semiconductor (CMOS), a photodiode (such as an avalanche photodiode), solid state photomultiplier tube (PMT), image receptor, or a camera for measuring reflected light from the sample over a selected range of wavelengths. Typically, a photodetector (such as a photodiode) may be employed when using monochromatic light, and the spectrometer, or CCD, or a camera may be employed when using the broadband light. In embodiments where the detector 58 is a CCD or a camera, the detector 58 may record the spectrum of the reflected light from the sample. For each of the samples 30 on the detection surface 22 there is a corresponding column or row in the 2D spectrometer to measure the interference spectrum of the corresponding sample on the detection surface 2. If the imaging is done in a y-direction on the imaging surface 22 (which is e.g., a direction of columns), the different samples in a column are individually identified. However, for the samples 30 disposed in x-direction (which is e.g., a direction of rows) the different samples in a row are separately identified by introducing a phase difference using the phase difference generator 50. After imaging using the Fourier transform, the samples 30 in the 2D array of samples are individually identified by the detector.

The imaging spectrometer may be coupled to detection circuitry that may form part of the signal processing unit 60. In one example, the detection circuitry may convert current signal to voltage signal. Also, the detection circuitry may amplify the signal received from the imaging spectrometer 54. The detection circuitry may include components, such as but not limited to, data processor, for receiving measurements of interference pattern from the detector 58, such as a spectrometer, and for conducting analysis thereon, wherein the analysis comprises determining a parameter of an interference spectrum. Non-limiting examples of such parameters may include frequency, phase, and intensity of the interference fringes.

A computer (not shown) may be used to process and display the signals and may form part of the signal processing unit 60. The computer may be used to generate a variety of quantitative and qualitative measures. For example, in quantitative measurements, the abscissa may represent time and the ordinate may represent percentage of concentration of an analyte. In addition, the computer may have a spectrum library, which stores the information regarding the spectral characteristics of various elements or chemical compounds. This spectrum library may be used to identify unknown samples by comparing the spectral information received from an unknown sample with spectral patterns retained in the library, and identification of the unknown substance may be made by comparison.

Although not illustrated, in one embodiment, an image stabilization unit may be coupled to the optical engine 16 for stabilizing the image by countering, reducing or eliminating the environmental noise. For example, temperature stabilizing, or fringe locking the cavity may reduce or minimize the systematic noise like temperature noise, or mechanical noise. In another embodiment, the SNR may be improved by either integrating or averaging the signal over time. The SNR may also be improved by temperature stabilizing the detection surface.

An example of a phase difference generator is shown in FIG. 3. In this example, the phase difference generator 62 comprises a wedge shape having a number of steps 64, 66 and 68. The resultant sample radiation or the reference beams, generally represented by reference numerals 70, 72 and 74, pass through the steps 64, 66 and 68, respectively. The beams 70, 72 and 74 travel through different thicknesses in the medium of the phase difference generator 62. The different path lengths traversed by the beams 70, 72 and 74 in the medium of the phase difference generator 62 results in a path length difference being introduced in the beams 70, 72 and 74. The path length difference is translated to phase difference, which enables each of the three different beams 70, 72 and 74 being recognized separately in the image.

The different sample fields in a direction parallel to the steps 64, 66 and 68 are spectrally separated by the phase difference generator 62. Whereas, the different samples in a direction perpendicular to the steps 64, 66 and 68 are imaged on to a spectrometer. The number of steps may depend on the number of samples disposed in that x-direction so that each of the steps corresponds to a sample. The phase difference generator 62 may be made of materials, which have a refractive index higher than that of the medium (such as air) through which the reference beam, or the sample beam, or the resultant sample beam traverses. The material of the phase difference generator is transparent to the reference beam, or the resultant sample beam. Non-limiting examples of the materials for the phase difference generator may include glass, polymer, a dielectric material, and other like materials. The phase difference generator may be made of a dielectric material, a multilayer dielectric coating, a stack of glass plates, a liquid crystal display, or a sandwich structure of different refractive index materials.

Although illustrated as steps, the phase difference generator may have other geometrical shapes, such as but not limited to microelectromechanical systems (MEMS) based phase plate, liquid crystal phase modulator, wave plate, to create a path difference. Further, in some embodiments, the phase difference generator may include phase difference inducing features along y-direction. In these embodiments, a relative phase difference may be introduced between the reflected sample beam and a reference beam in both x- and y-directions (rows and columns of the 2D array of samples).

FIG. 4 illustrates a phase difference generator 76, which comprises patterned structures 78 and 80. The patterned structure 78 may have in-built steps of a first material having a first refractive index. The patterned structure 80 having steps of a second material having a second refractive index is coupled to the patterned structure 84. Both the structures 78 and 80 may be coupled to form a planar structure. The planar structure has a refractive index gradient that increases or decreases while traversing from one end to the other of the phase shift component 76.

FIG. 5 illustrates a phase difference generator 82 having a patterned structure. The phase difference generator 82 may comprise patterns 84, 86 and 88. Each of the patterns 84, 86 and 88 may have a refractive index that is different from the refractive indices of the remaining patterns. The refractive index of the patterns 84, 86 and 88 may gradually increases or decreases while traversing from one end of the phase shift component 82 to the other. The size of the patterns may be determined based on the size of the samples so that each of the patterns 84, 86 and 88 corresponds to a single row or column of samples in the 2D array. The patterns 84, 86 and 88 may be made of one or more materials. In one example, the patterns 84, 86 and 88 may be made of two materials, with the percentage volume of the materials being different in the different patterns to obtain refractive indices that are different from each other.

The detection system of the invention may be used in different detection techniques to obtain a one-shot/simultaneous detection for 2D array of samples. The detection surface may be modified depending on the different applications. Also, other arrangement, such as relative position of the camera and the detector may be changed based on the application.

In certain embodiments, an SPR imaging system is provided for simultaneous detection and imaging of two or more samples. For example, the SPR imaging system may be used to detect a concentration of one or more analytes, such as biomolecules, or a rate of association and/or dissociation of one or more analytes in an analyte solution. In certain embodiments, a 2D array is provided for simultaneous detection of concentration of two or more different analytes in a solution, or a concentration of a single analyte from two or more different analyte solutions. The multi-analyte format can also be used to detect the rate of reaction of the analytes in the solution. In one embodiment, the SPR imaging system employs a broadband light source so that SPR curves in different wavelengths may be measured in a single shot image for a 2D array of samples.

Figure 6:
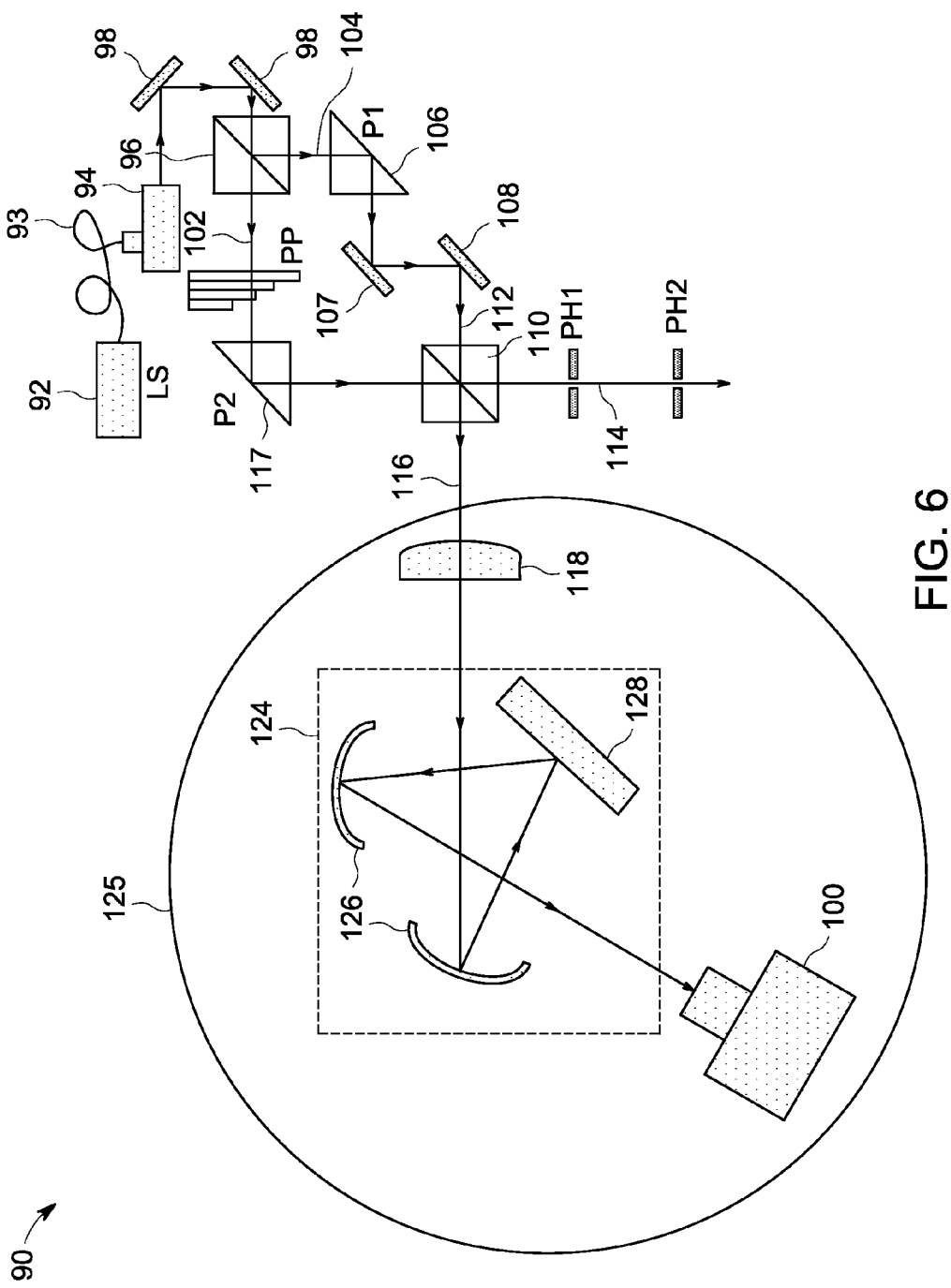
FIG. 6 is a schematic diagram of an embodiment of a 2D SPR imaging system of the invention for simultaneous detection and imaging of a 2D array of samples.

FIG. 6 illustrates an example of a 2D SPR imaging system 90 for detecting and imaging a 2D array of samples. The system 90 comprises a broadband light source 92 for emitting broadband radiation. The radiation source 92 is optically coupled to the collimator 94 using optical fiber 93. The collimated radiation from the collimator 94 is directed to a beam splitter 96 using mirrors 98. The beam splitter 96 divides the collimated radiation into two beams 104 and 102. Phase difference is induced in the reference beam 102 using a phase difference generator 115. The reference beam 102 is directed to an imaging spectrometer 125 using a right angle prism 117. Optionally, the beam splitter 110 splits the reference beam 102 into two portions.

The second portion 104 of the collimated radiation is incident on a SPR surface 106. In one example, the surface 106 is a thin metal film coated prism having a detection surface (not shown) having a 2D array of samples. The sample beam 104 undergoes internal reflection in the prism 106 and is reflected off of the thin metal film and out of the sample fields on the SPR surface 106. The thin metal film may comprise gold, silver or copper. The prism may be made of glass, although various other materials having suitable optical properties for internally reflecting the incident beam and transmitting the reflected SPR beam may also be used. The resultant sample beam from the SPR surface 106 is directed to the imaging spectrometer 125 using optics comprising mirrors 107 and 108.

In one embodiment, the material of the definer component and the metal required for SPR phenomenon may be selectively disposed/patterned onto the detection surface or the SPR surface 106. That is, certain portions of the SPR substrate that are configured to receive the sample may include gold, while the other portions may not include gold, but may include the material of the definer component. Sample radiation may be incident onto the thin metal film.

At the beam splitter 110, a portion of the reference beam 102 having the phase difference induced by the phase difference generator 115 and a portion of the resultant sample beam 112 interfere and produce an interference spectrum. At beam splitter 110 a condition is thus created under which interference between the reference beams and the reflected sample beams can occur giving rise to intensity variations of the beam emerging from the SPR surface 106. The reference beam 116 is received by an imaging spectrometer 125. The spectrometer 125 comprises a detector 100, a grating 128 and one or more optical elements, such as a cylindrical lens 118. The interference beam 116 passes through the cylindrical lens 118 and is received by the monochromator 124. In the illustrated embodiment, the monochromator 124 comprises cylindrical mirrors 126 and a grating 128. The reflected light from the monochromator 124 is received by the detector 100.

The phase difference introduced in the reference beam 102 is present in the interference beam 116. The interference beam 116 passes through the grating 128, which may split and diffract the interference spectrum into different wavelengths of light. The different wavelengths of light are then incident on the detector 100.

At the imaging spectrometer 125, the interference spectrum may be measured as a function of the path difference. Because of the effect of this interference, the intensity of the beam passing to the detector 100 depends on the difference in the path length of the reference beam 98 and the resultant sample beam 112. Optionally, for alignment purposes a portion of the interference spectrum may be directed through pinholes 118 and 120 to be received by a reference detector (not shown).

The detection surface of the SPR arrangement may comprise 2D array of samples disposed in the form of a patterned thin layer. The samples may be disposed on a thin metal film disposed on a glass substrate. In contact with the surface of the thin metal film may be one or more flow cells for delivering the samples for depositing on the thin metal film in the form of patterned thin layer.

The SPR imaging system 90 may include a generally closed housing having an exit beam port therein to direct the beam at the imaging spectrometer 125. The broadband light source may be disposed within the housing, and the detector may be disposed outside the housing. In the SPR imaging system 90, gratings may be used in place of the prism 117. Each of the samples may have a corresponding grating disposed on the SPR substrate 108.

The imaging spectrometer 125 may be operatively coupled to signal processing unit that measures interference spectra acquired by the detector. In one embodiment, the wavelength sensitivity of the resonance may be exploited by keeping the angle of incidence fixed, and measuring the SPR effect as a function of wavelength. The reflectance spectrum exhibits a pronounced minimum due to the SPR effect in the visible to near infrared to infrared wavelengths. The position of the reflectance minimum may be varied by changing the metal film thickness. In one embodiment, the position of the reflectance minimum shifts in wavelength upon the adsorption of sample molecules onto the metal surface due to the change of index of refraction at the sample-gold film interface. The detection system of the invention can be used to study the adsorption onto a chemically modified metallic surface from the gas phase as well as from liquid solutions. In particular, the adsorption of biological molecules such as DNA, proteins, antibodies, and enzymes from aqueous solutions can be monitored in situ with the detection system. Advantageously, the detection system of the invention provides wavelength stability and measurement reproducibilty, fast data acquisition rates and high signal-to-noise outputs, and broadened spectral range.

Figure 7:
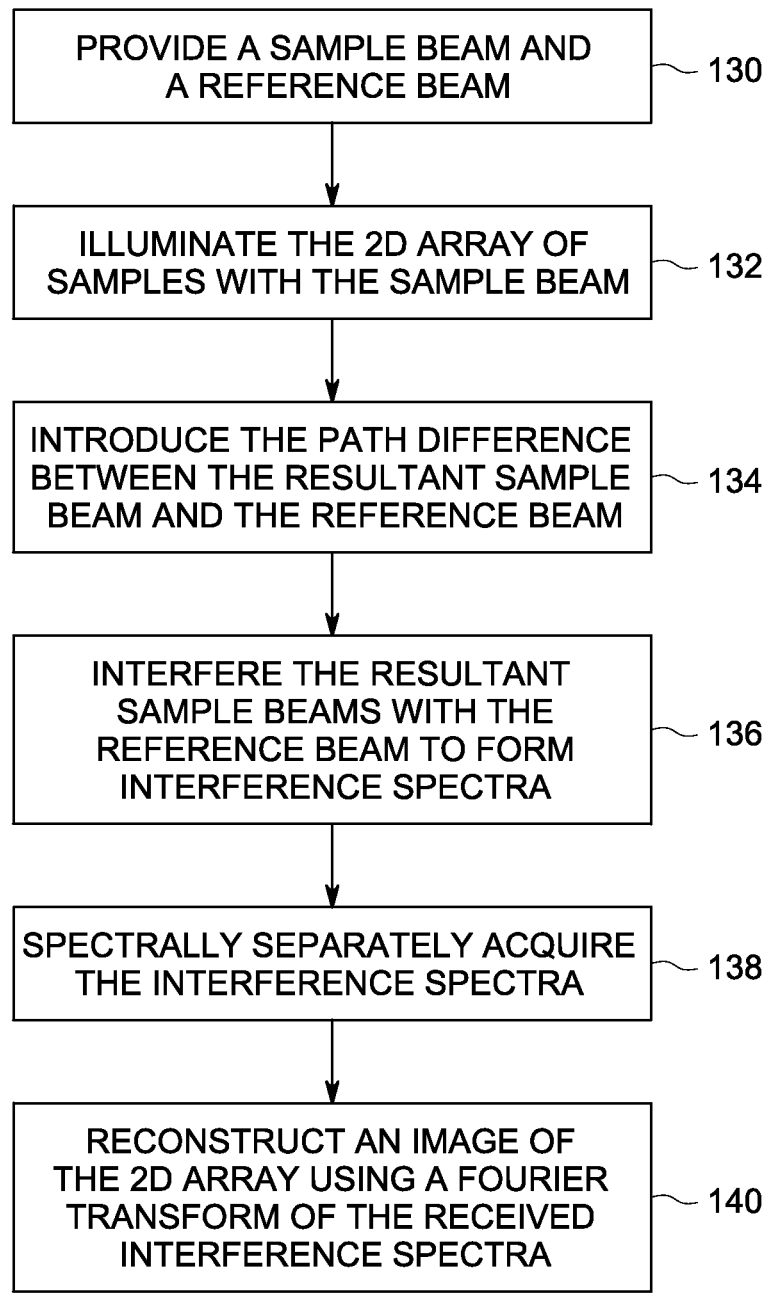
FIG. 7 is a flow chart of an example of a method of the invention for simultaneous detection and imaging of 2D array of samples.

FIG. 7 illustrates an example of a method for simultaneous detection and imaging of 2D array of samples. At step 130, a sample beam and a reference beam are provided. The sample beam and the reference beam may be provided by a single source, such as a broadband light source. The beams may be divided into a sample beam and a reference beam using a beam splitter. At step 132, the samples in the 2D array are illuminated with the sample beam. The resultant sample beam from the samples may be a reflective or transmissive beam. At step 134, a determined path difference is introduced in the resultant sample beam or the reference beam. The path difference may be introduced in a direction that is perpendicular to a ruling direction of the grating 128. In one example where the path difference is introduced in the resultant sample beam, relative path differences may be introduced between the resultant sample beams from the samples of a particular row. Assuming that the direction of traversing the samples in a row is x-direction, which is also a direction perpendicular to the ruling direction of the grating. The phase difference generator may be disposed such that the portions of the phase difference generator having different paths are parallel to the x-direction. In this way, the samples disposed in a particular row will have a path length difference induced in their corresponding sample beams. However, samples of a particular column may or may not have a relative path difference introduced due to the phase difference generator. In cases where relative path difference is not introduced in the samples of a column, sample beams from the samples of a particular row will traverse similar distance inside the phase difference generator to reach the detector. The samples of a particular column may be spectrally resolved using a 2D detector. At step 136, a condition for interference is generated between the resultant sample beam and the reference beam. At step 138, the interference spectra is spectrally separately acquired. The spectral difference may be produced by passing the interference spectra through a grating before receiving the spectra by a 2D detector. At step 140, an image of the 2D array is reconstructed using a Fourier transform of the received interference spectra. Advantageously, introducing the path length difference (which translates to phase difference), the different samples on the 2D array are separately identifiable in the reconstructed image using the induced path length difference.

Figure 8:
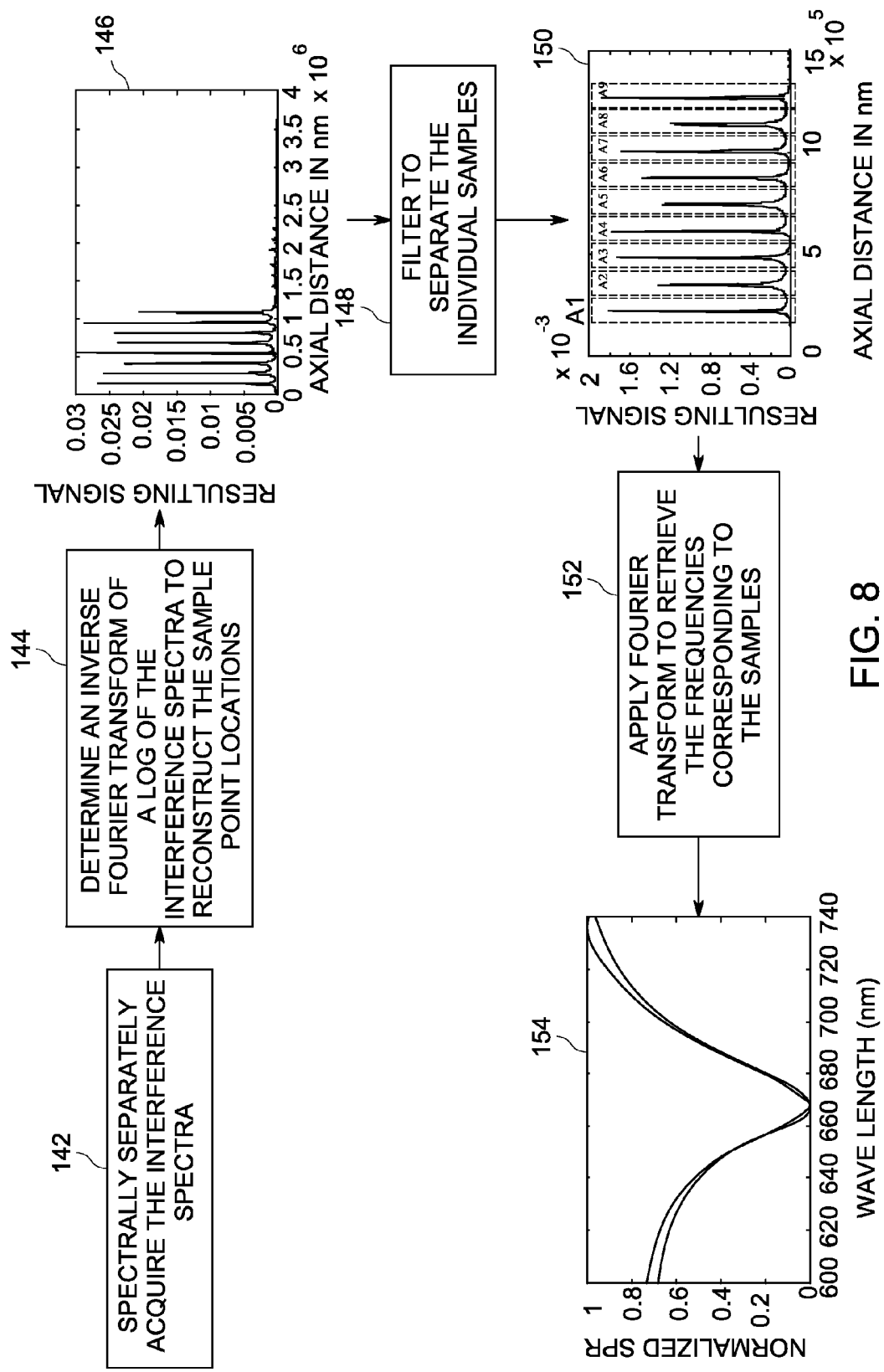
FIG. 8 is a flow chart of an example of a method of the invention for reconstructing an image of the 2D array.

FIG. 8 provides an example of steps involved in reconstructing an image of the 2D array. After acquiring the interference spectra, which is spectrally separated, at step 142, at step 144, an inverse Fourier Transform is performed on the interference spectrum to reconstruct the sample points (as illustrated by reference numeral 146). At step 148, filtering is performed to separate the individual sample points depending on the frequency. In one embodiment, as illustrated by reference numeral 150 a windowing technique may be used to spectrally separate the individual sample points. In another embodiment, at step 142 may be analyzed using time frequency analysis to determine spectra and/or content of the different sample points. At step 152, a Fourier Transform is determined to retrieve the frequencies corresponding to the different spatial positions (i.e., the samples). At step 154, the frequencies may be converted to wavelengths to determine the amount of absorption (e.g., SPR dip), or transmission.

Figure 9:
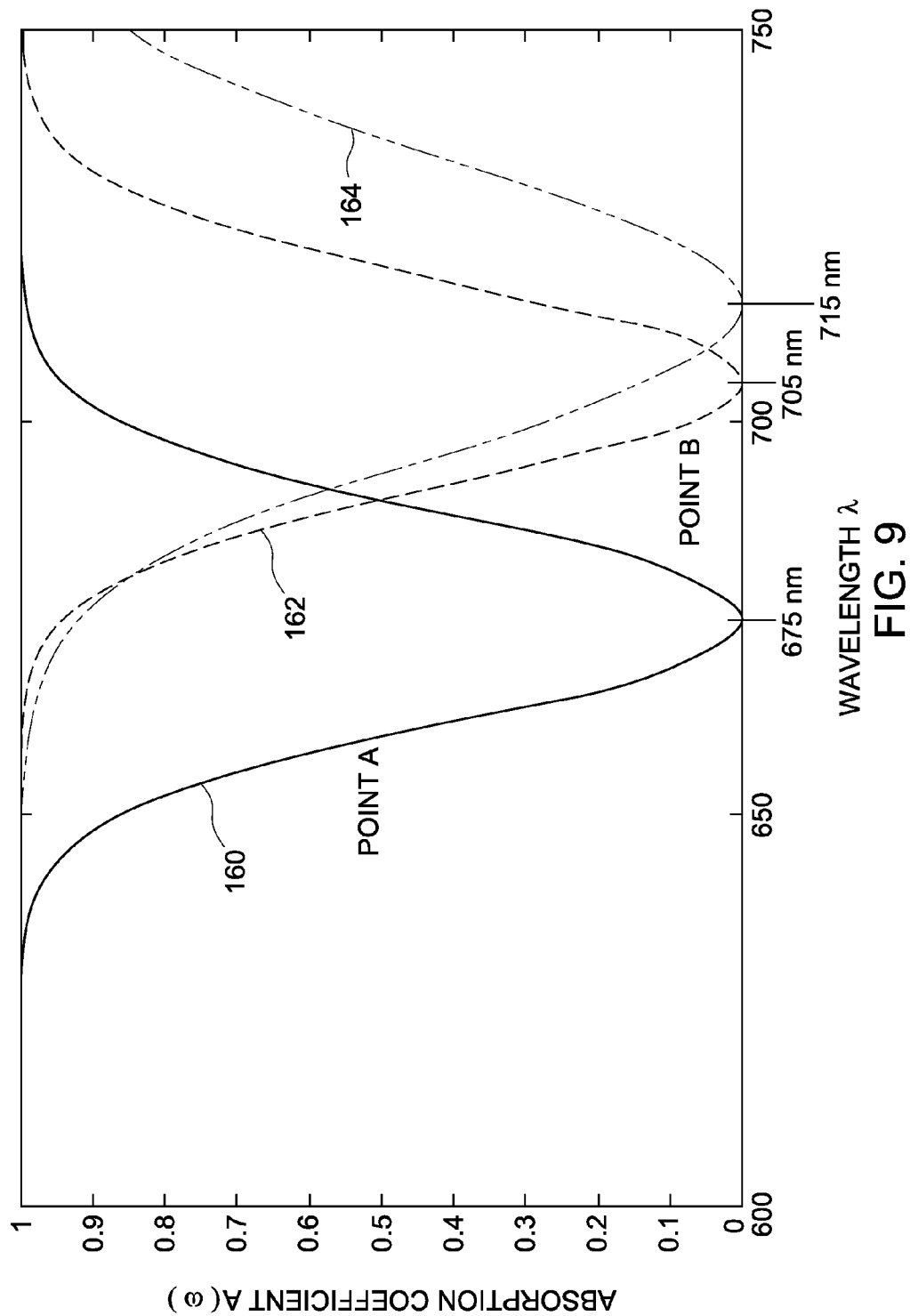
FIG. 9 is a graph of examples of simulation results for Gaussian profiles of absorption coefficients for three points on a detection surface FIG. 10 are graphs corresponding to the three points of FIG. 9 for which inverse Fourier transform is calculated.
Figure 10:
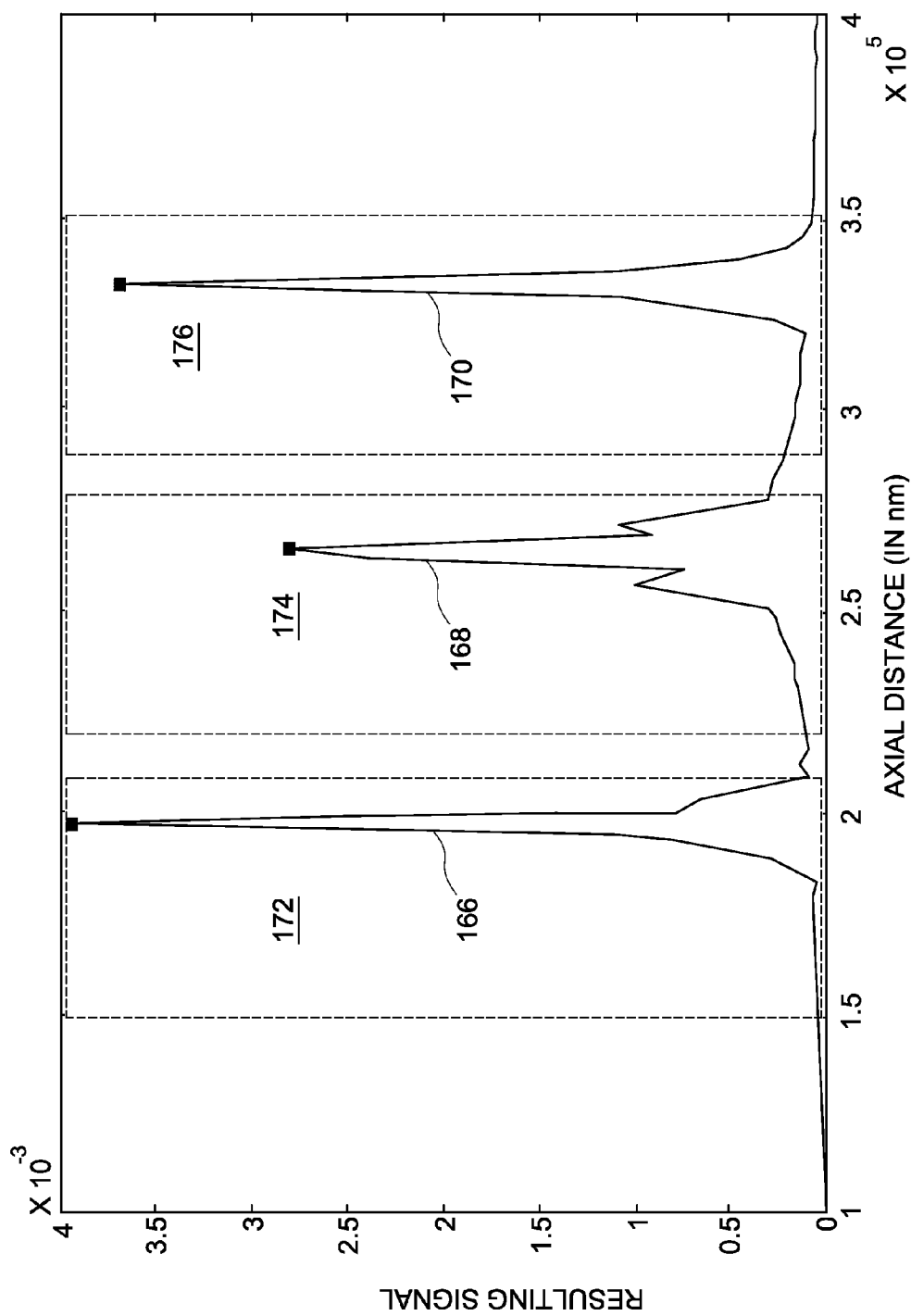
Figure 11:
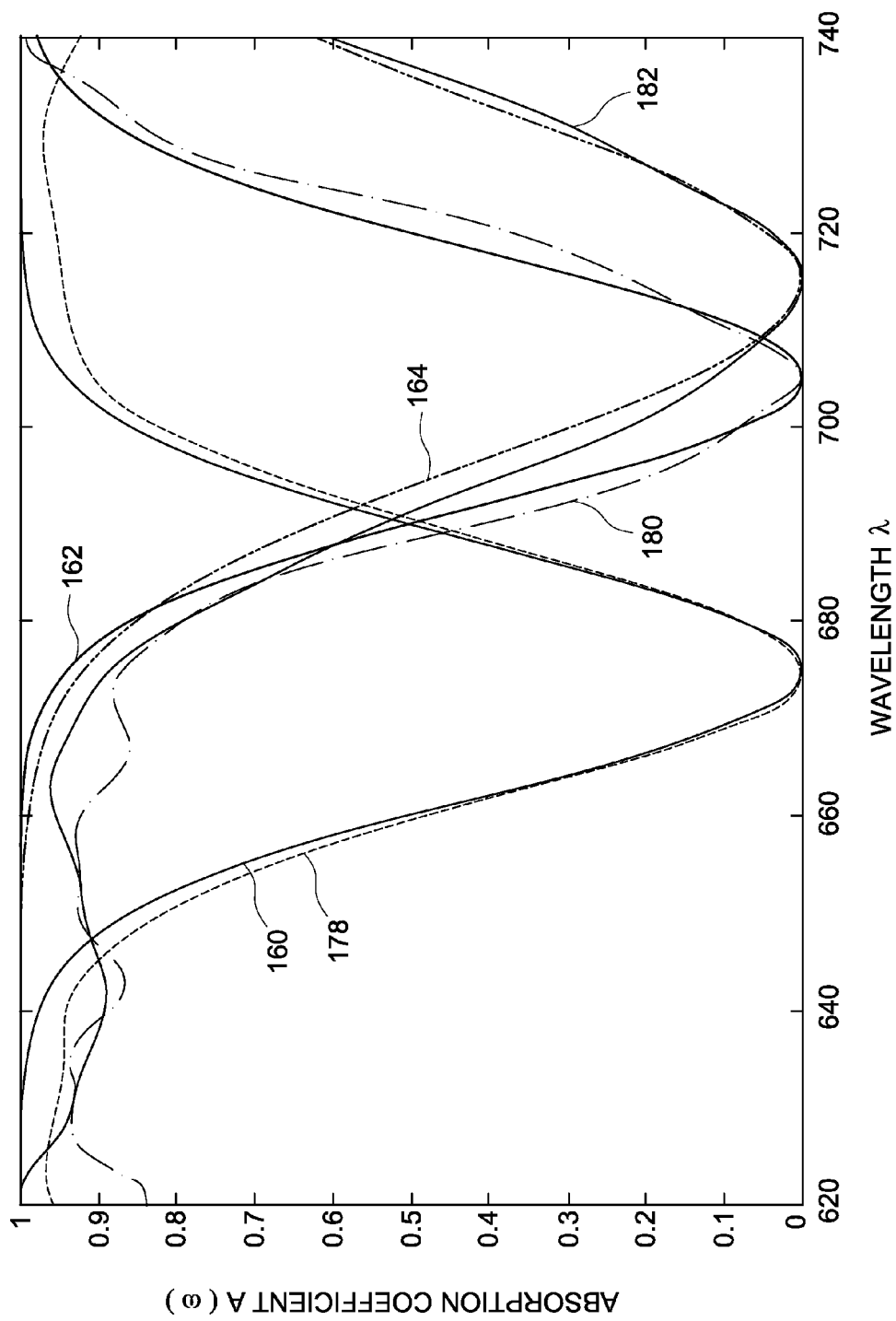
FIG. 11 are graphs for retrieved SPR for the three points of FIG. 9.

FIGS. 9-11 illustrate simulation results for image reconstruction for three points on a detection surface. It is assumed that the samples at a first point and a second point have SPR phenomenon at 675 nm and 705 nm, respectively. It is further assumed that the third point is a buffer that has a SPR at 715 nm. A first point and a second point are at a distance of 0.0678 mm, and the first point and a third point are at a distance of 0.135 mm. FIG. 9 illustrates Gaussian profiles of absorption coefficients for the three points, curve 160 represents the Gaussian profile for the first point, curve 162 represents the Gaussian profile for the second point, and curve 164 represents the Gaussian profile for the third point which is a buffer. The three curves show the dips at SPR wavelength. That is, for the first point (curve 160) the SPR dip is at 675 nm, for the second point (curve 162) the SPR dip is at 705 nm, and for the third point (curve 164) the SPR dip is at 715 nm. Using the numerical simulation and the signal processing approach, the retrieved spatial distance between samples or points is determined.

FIG. 10 illustrates curves 166, 168 and 170 that correspond to first, second and third points, respectively. The three dotted rectangles 172, 174 and 176 represent regions in the SPR curves 160, 162 and 164 (see FIG. 9) for which inverse Fourier transform is calculated. Spatial positions for the three points are retrieved by calculating the inverse Fourier transform. In one embodiment, a windowing technique may be performed to separate the spatial positions.

FIG. 11 shows the retrieved SPR for the three points. Once the three points are isolated (as shown in FIG. 8), a Fourier transform is performed to retrieve the frequencies corresponding to the three spatial positions. These frequencies are subsequently converted to wavelength in order to determine the SPR dip. In the illustrated embodiment, the retrieved SPR curves 178, 180 and 182 corresponding to the first, second and third point, respectively, on the detection surface are shown in comparison with original SPR curves 160, 162 and 164. During processing, re-sampling of the data may be done to remove the nonlinearity in the data.

Although the invention is discussed mainly with reference to SPR technique, in one embodiment, the technique may be applied to a reflectometric interference spectroscopy (RIfS) to analyse a 2D array of samples. In this embodiment, a phase difference generator may be disposed in the beam path of either the resultant sample beam or a reference beam is a physical method based on the interference of broadband light at thin films, which may be used to investigate molecular interaction. RIfS, like SPR is a label-free technique, which allows the time-resolved observation of interaction among the binding partners without the use of fluorescence or radioactive labels. While the detection is based on phase change in case of free solution, and RiFS, for LSPR and nano-structured gating SPR the detection is based on spectral changes.

In one embodiment, the detection surface may be regenerated to allow the detection system to be used over and over again, thereby reducing the working material required, with a consequent significant cost reduction.

In certain embodiments, the one or more sample fields of the detection surface that are immobilized with ligands may saturate due to high concentrations of the samples, or due to exposure of the detection surface to the sample solution for a long period time. In these embodiments, the detection surface needs to be regenerated to further detect the samples. In one example, the regeneration of the detection surface may be achieved by applying a different solution than previously used. In one example, the detection surface may be exposed to a base solution, such as sodium hydroxide, or to an acidic solution, such as, glycine hydrogen chloride buffer having pH 2.0, to regenerate the detection surface. The regeneration of the ligands considerably reduces the cost of the sensor assembly. In one embodiment, regeneration of the ligands enables detection of different sample solutions. In this embodiment, the ligands are regenerated after detecting an sample solution, and before flowing the next sample solution in the fluidic channels.

No mechanical moving parts gives instrument longer lifetime and relative immunity to mechanical vibrations. Large number of SPR curves for 2-D array of sample fields can be imaged in a single shot. The Fourier transform approach to 2D SPR provides high signal-to-noise outputs, high wavelength precision, and reproducibility, and high ordinate precision. Single shot imaging allows higher frame rates in data gathering improving SNR.

The detection system of the invention may be used in determination of active concentration, screening and characterization in terms of both affinity and kinetics. Unlike fluorescence and chemiluminescence methods no dye-marked samples and also no antibodies are needed in SPR for the protein to be tested.

The optical sensing device may be used in a variety of applications, for example, in molecular biology and medical diagnostics where specific binding of bioactive molecules to their corresponding binding partners, for example, DNA, proteins, need to be determined. Based on the electrical detection of specific molecular binding events, the affinity sensor may be used to monitor, for example, molecules, viruses, bacteria, and cells in the most diverse samples, such as clinical samples, food samples, and environment samples such as, plants, whereby such monitoring is performed in a time efficient manner. The optical sensing devices may be used in the fields of molecular detection and concentration analysis of biomolecules, kinetic and equilibrium analysis of biochemical reactions, control of fermentation processes, evaluation of ligand-cell-interactions, clinical analysis, and cell demotion. In certain embodiments, the optical sensing device may be used in the molecular biology field, for example, in medical diagnostics, biosensor technology or DNA-microarray technology, for detecting specific molecular binding events.

Advantageously, the monitoring or detection can be performed in real-time. For example, binding reactions may be monitored in real time, thereby reducing cost. The principles and practice of the methods described and claimed may be used to analyze any binding reaction, including, but not limited to, those involving biological molecules. For antibody binding affinity measurements, an antigen typically is immobilized on the sensing surface. That surface then is exposed to a solution containing the antibody of interest, and binding proceeds. Once binding has occurred, the sensing surface is exposed to buffer solution (e.g. one that initially has no free antibody) and the dissociation rate is continuously monitored in real time. One or more embodiments of the sensing device are a low cost and simple optical sensing device. In addition, the devices can be used for multiple-point sensing, thus providing a high throughput.

EXAMPLES

A hyper-spectral reconstruction of SPR of a 4×4 sample array is provided. The experimental setup used to reconstruct SPR spectra comprises of a 4×4 array of samples disposed on a gold-coated prism surface. The experimental setup comprised of Mach Zehnder configuration. A Xenon Arc Lamp Model FL-1039/40, manufactured by HORIBA Jobin Yvon Inc. (3880 Park Avenue, Edison New Jersey N.J. 08820-097 USA) is used as a light source. A 200 microns core multimode fiber is coupled to the light source. The fiber is connected to fiber collimator, which produces beam having a diameter of about 12 mm. A linear polarizer is placed in path of the beam from the fiber collimator. The linear polarizer is oriented so as to produce SPR in gold-coated prism. The SPR phenomenon is produced in a gold-coated prism using linearly polarized light. The SPR is incident on the gold-coated prism at an incidence angle of about 45 degrees. Ocean Optics Spectrometer Model No. SD2000 (830 Douglas Ave., Dunedin, Fla. 34698, USA) is used to collect light in the path of pinholes with reference arm being blocked. SPR phenomenon is observed for this setup, however, the SPR phenomenon disappeared when polarizer is rotated by 90 degrees, thereby confirming the existence of the SPR. Combined beams from the interferometer are focused by cylindrical lens on to a spectrometer slit. The slit served to restrict spot size of the interference beam on the camera for achieving high quality fringes. A Triax 180 imaging spectrometer obtained from Horiba (Ocean Optics Spectrometer, HORIBA Jobin Yvon Inc, 3880 Park Avenue, Edison New Jersey N.J. 08820-097 USA) is used for resolving the signal in Fourier domain.

For reconstructing SPR in a 2D spot area a phase plate 190 is introduced in the path of the beam 192 as shown in FIG. 12. The phase plate 190 is made up of four glass slides 193, which divides beam area in to four regions 194. Four different optical thicknesses of the glass slides 192 reconstruct distinct SPR of the four regions 194 simultaneously.

FIG. 13 illustrates four regions 194 produced by phase plate artificially divided in to further four rows to produce 4×4 spot array 196 in the beam cross-section. 60 images of the interference image were collected. The 60 images are processed to produce inverse Fourier Transform image with four peaks corresponding to four spots columns. The spot columns are divided into four rows, and a Fourier Transform of the individual peaks is performed to determine spectral absorption at each spot location.

Figure 14:
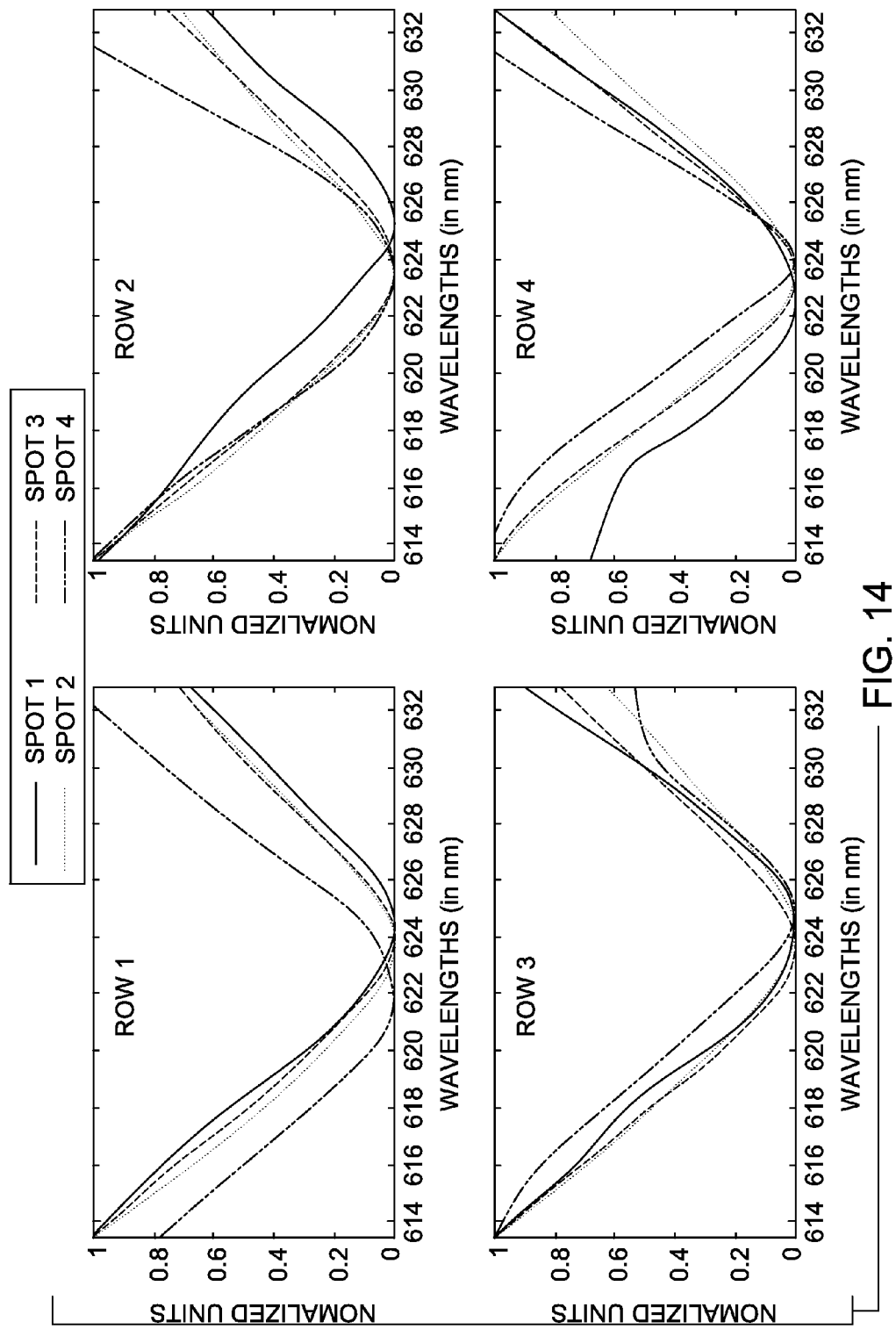
FIG. 14 are graphs of spectral absorption obtained after filtering and Fourier transforming individual spots of the 4×4 spot array.
Figure 15:
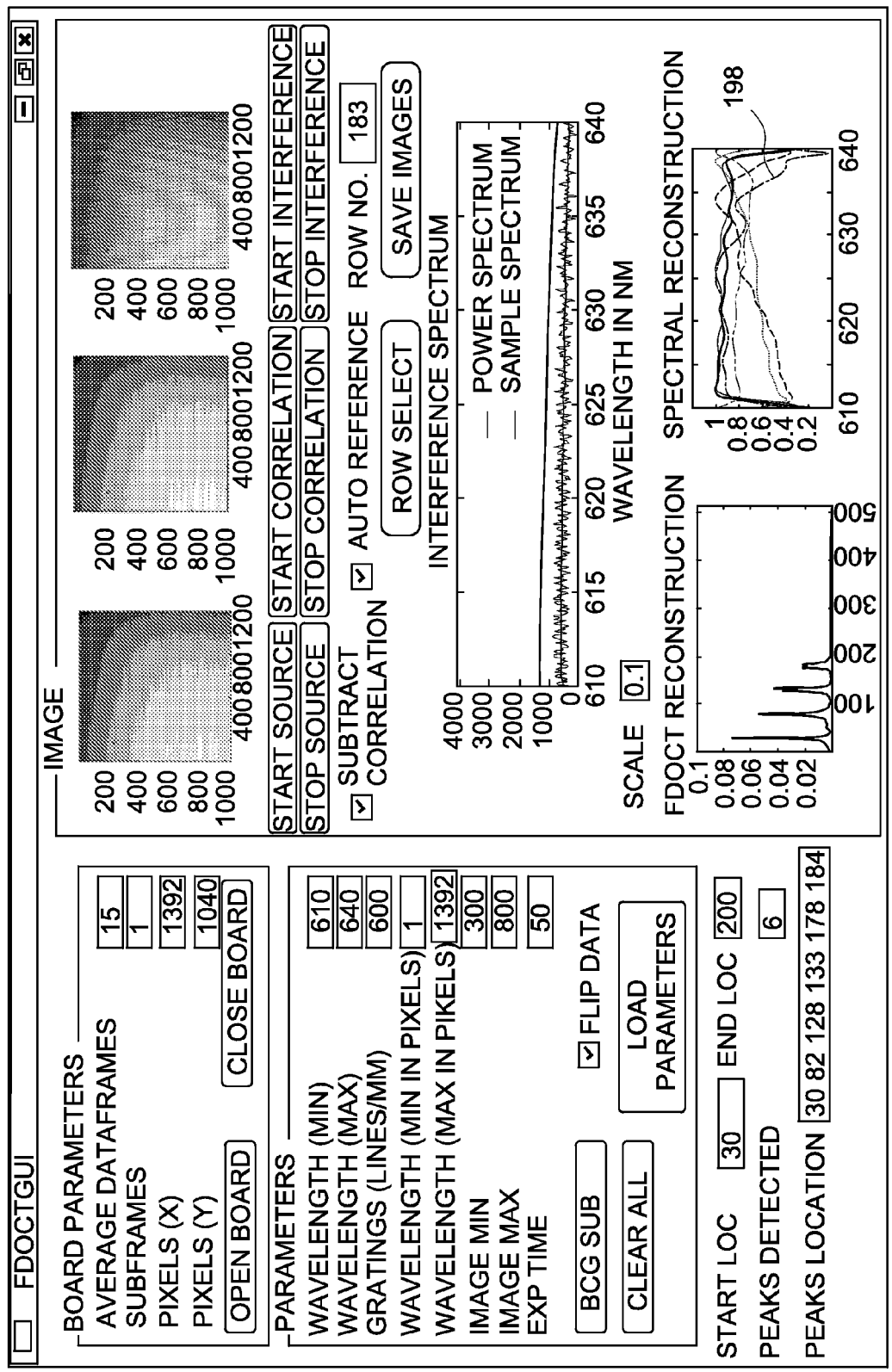
FIG. 15 is a pictorial drawing of a user interface illustrating a characteristic SPR dip in the spectra when a linear polarizer is rotated by 90 degrees.

FIG. 14 illustrates the spectral absorption obtained after filtering and Fourier transforming individual spots 4×4 spot array 196. Qualitatively, a close resemblance is observed between the response obtained using the Ocean optics spectrometer and the responses shown in FIG. 14 for rows1-4 and spots1-4. FIG. 15 illustrates spectra when a linear polarizer is rotated by 90 degrees. A characteristic SPR dip is observed as illustrated in the graph 198.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A detection system for interferometric spectral imaging of a two-dimensional (2D) array of samples, comprising:
    a broadband light source;
    a detection surface having a plurality of sample fields configured to receive a two-dimensional array of samples, wherein one or more portions of the detection surface comprise a metal film having gold, and wherein the broadband light source is configured to provide light to the detection surface at an incidence angle configured to produce a surface plasmon resonance phenomenon;

a phase difference generator configured to resolve the sample fields of the plurality of sample fields, wherein the phase difference generator is configured to generate a phase difference in a reference beam or a resultant sample beam by introducing a path length difference between the resultant sample beam and the reference beam;

an interferometer configured to combine the reference beam and the resultant sample beam; and an imaging spectrometer comprising a spectrally separated two-dimensional detector configured to receive the combined reference and resultant sample beams, and wherein the imaging spectrometer is configured to discriminate between two or more spatially separated points in the two-dimensional array of samples based on the combined reference and resultant sample beams.

2. The detection system of claim 1, wherein the phase difference generator is disposed in a path of the resultant sample beam.

3. The detection system of claim 1, wherein the phase difference generator is disposed in a path of the reference beam.

4. The detection system of claim 1, wherein the phase difference generator comprises a dielectric material, a stack of glass plates, or a liquid crystal display.

5. The detection system of claim 1, wherein the phase difference generator comprises portions having different thicknesses.

6. The detection system of claim 1, wherein the phase difference generator comprises a planar structure having a plurality of portions, and wherein each portion of the plurality of portions has a refractive index that is different from a refractive index of other portions of the plurality of portions.

7. The detection system of claim 1, wherein the detection surface comprises a thin metal film disposed on a substrate, nano-gratings disposed on a substrate, or the metal film having gold disposed on a glass substrate.

8. The detection system of claim 1, wherein the spectrally separated two-dimensional detector is operatively coupled to a grating.

9. The detection system of claim 8, wherein the grating comprises from about 150 lines per mm to about 3600 lines per mm.

10. The detection system of claim 1, further comprising a beam splitter operatively coupled to the broadband light source and configured to split a beam from the broadband light source into a sample beam and the reference beam.

11. The detection system of claim 1, further comprising a filtering component configured to at least partially absorb reflected light beams reflected from portions of the detection surface.

12. A two-dimensional surface plasmon resonance imaging system, comprising:
a surface plasmon resonance surface having a two-dimensional array of samples disposed in one or more corresponding sample fields;
a broadband light source that illuminates one or more of the sample fields;
a phase difference generator that introduces differences in pathlengths of resultant sample beams reflected from the two-dimensional array of samples; and
a detector that receives the resultant sample beams from the two-dimensional array of samples.

13. The two-dimensional surface plasmon resonance imaging system of claim 12, wherein the SPR surface comprises a metal film, or a nano-grating.

14. The two-dimensional surface plasmon resonance imaging system of claim 12, wherein the surface plasmon resonance surface comprises a gold film disposed on a glass substrate.

15. A method for simultaneous imaging of samples in a two-dimensional array of samples, comprising:
providing a sample beam and a reference beam using a broadband light source, wherein the sample beam is provided at an incidence angle configured to produce a surface plasmon resonance phenomenon;
illuminating the samples in the two-dimensional array of samples with the sample beam to produce a resultant sample beam, wherein the samples in the two-dimensional array of samples are disposed on a detection surface comprising a thin metal film;
introducing a path length difference in one of the reference beam or the resultant sample beam;
interfering the resultant sample beam with the reference beam to form interference spectra;
spectrally separately acquiring the interference spectra; and
reconstructing an image of the two-dimensional array of samples using a Fourier transform of the acquired interference spectra.

16. The method of claim 15, wherein the samples in the two-dimensional array of samples are illuminated at a constant angle, and wherein the constant angle is configured to produce the surface plasmon resonance phenomenon.

17. The method of claim 15, further comprising stopping a portion of the sample beam from reaching at least a part of non-sample regions disposed on the detection surface.

18. The method of claim 15, further comprising filtering at least a portion of light from the resultant sample beam, wherein the portion of light is reflected by non-sample regions disposed on the detection surface.

19. The method of claim 15, wherein reconstructing comprises:
determining the Fourier transform of the interference spectra;
filtering the interference spectra to spatially separate one or more curves corresponding to the samples of the two-dimensional array of samples;
applying an inverse Fourier transform to retrieve frequencies corresponding to spatial positions of the samples of the two-dimensional array of samples.

20. The method of claim 19, further comprising translating the frequencies to wavelengths.

* * * * *